US00PP33631P2

(12) United States Plant Patent
Hansen

(10) Patent No.: US PP33,631 P2
(45) Date of Patent: Nov. 9, 2021

(54) ***ECHINACEA* PLANT NAMED 'THE PRICE IS WHITE'**

(50) Latin Name: ***Echinacea* hybrid**
Varietal Denomination: The Price Is White

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,292

(22) Filed: Dec. 18, 2020

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428, 226
CPC ... A01H 5/02; A01H 5/00; A01H 6/14; A01H 6/1448
See application file for complete search history.

(56) References Cited

U.S. PATENT DOCUMENTS

PP19,441 P2 * 11/2008 Korlipara ..... A01H 6/14 Plt./428
PP21,790 P2 * 3/2011 van den Aardwegh . A01H 6/14 Plt./428

OTHER PUBLICATIONS

Winter/Tribune News Service Post-Gazette 2020, retrieved on Apr. 7, 2020, retrieved from the Internet at https://www.post-gazette.com/life/garden/2020/10/23/On-Gardening-Color-Coded-coneflowers-Norman-Winter-Price-Is-White/stories/202010250011, 2 pp. (Year: 2020).*

* cited by examiner

*Primary Examiner* — June Hwu

(57) ABSTRACT

The new and distinct cultivar of *Echinacea* plant named 'The Price Is White', with fragrant inflorescences on strong well-branched stems producing single whorls of broadly-overlapping, long, broad, white, ray florets that maintain their coloration with little change through maturity. The new plant is vigorous and produces a compact habit and flowers from mid-summer to fall frost with large fragrant inflorescences having a single row of large, broad, white, overlapping ray florets. The new plant is attractive and suitable as a potted plant, for the landscape, and for cut flower arrangements.

1 Drawing Sheet

Botanical denomination: *Echinacea* hybrid.
Cultivar designation: 'The Price Is White'.

STATEMENT REGARDING PRIOR DISCLOSURES UNDER 37 CFR 1.77(b)(6)

The first non-enabling disclosure of the claimed plant, in the form of a photograph and brief description was on a website operated by Walters Gardens, Inc. on Dec. 1, 2019. *Echinacea* 'The Price Is White' was listed with a photograph and brief description in the "Walters Gardens 20-21 Catalog" distributed first on May 20, 2020. The claimed plant was first sold on Mar. 2, 2020 by Walters Gardens, Inc., who obtained the plant and all information relating thereto, from the inventor. No plants of *Echinacea* 'The Price Is White' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'The Price Is White'. The new plant was the result of a cross on Jul. 15, 2016 by the inventor between the proprietary hybrid known only by the breeder code as 14-6-31 (not patented) as the female parent and 'Butterfly Kisses' U.S. Plant Pat. No. 24,458 at a wholesale perennial nursery in Zeeland, Mich. This single seedling selected was evaluated first in trials in the summer of 2017 at the same nursery and assigned the breeder code of 16-48-1. *Echinacea* 'The Price Is White' has been asexually propagated at the same nursery by crown division since 2017 and also using careful shoot tip tissue culture procedures and found to reproduce plants that exhibit all the characteristics identical to the original plant.

*Echinacea* 'The Price Is White' is distinct from all other Coneflowers known to the inventor. The nearest comparison cultivars are: 'TNECHKW' U.S. Pat. No. 30,856, 'Fragrant Angel' U.S. Plant Pat. No. 16,054, 'Alaska' U.S. Plant Pat. No. 17,547, 'Virgin' U.S. Plant Pat. No. 18,684, 'Purity' U.S. Plant Pat. No. 19,441, 'Milkshake' U.S. Plant Pat. No. 20,594, 'Heavenly Dream' U.S. Plant Pat. No. 21,957, 'White Mist' U.S. Plant Pat. No. 21,790, 'Little Angel' U.S. Plant Pat. No. 21,870, 'Polar Breeze' U.S. Plant Pat. No. 21,630, and 'White Swan' (not patented).

The female parent plant, 14-6-31, was taller in habit, with orange ray petals that were narrower. 'Butterfly Kisses' has a slightly shorter habit, anemone-type inflorescences and ray and disk florets that are light pink.

'TNECHKW' has shorter habit, with smaller inflorescences and fewer ray florets and the cones are more greencolored. 'Fragrant Angel' is taller and more upright in habit and the cone is more green. 'Alaska' is similar height with narrower habit, less branching with fewer inflorescences per stem and fewer and larger ray florets. 'Virgin' has smaller inflorescences on taller plants and the ray petals are a more chartreuse-white. 'Purity' has a taller and wider habit with less branching and fewer smaller flowers per plant. 'Milkshake' has a much larger habit, with significantly smaller anemone-type inflorescences. 'Heavenly Dream' has a larger habit with ray petals that are more drooping. 'White Mist' has more oranaish-yellow receptacle spines and narrower more drooping ray florets. 'Little Angel' is smaller in habit and the inflorescences are much smaller. 'Polar Breeze' is shorter in habit and the inflorescences are much smaller. 'White Swan' is seed cultivar that is taller in habit and ray florets are less horizontal with fewer ray florets per inflorescence and less branching per stem.

SUMMARY OF THE INVENTION

*Echinacea* 'The Price Is White' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong heavily-branched stems;
2. Large, broad inflorescences with single whorl of ray florets that tend to stay horizontal once open;
3. Ray petals are wide and broadly-overlapping;
4. Ray petals of clear white with orangish-yellow cones;
5. Vigorous growth and excellent habit;
6. Large, greyish-olive-green, lanceolate foliage.

BRIEF DESCRIPTION OF THE DRAWINGS

The photographs of the new invention demonstrate the overall appearance of the plant including the unique traits. The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
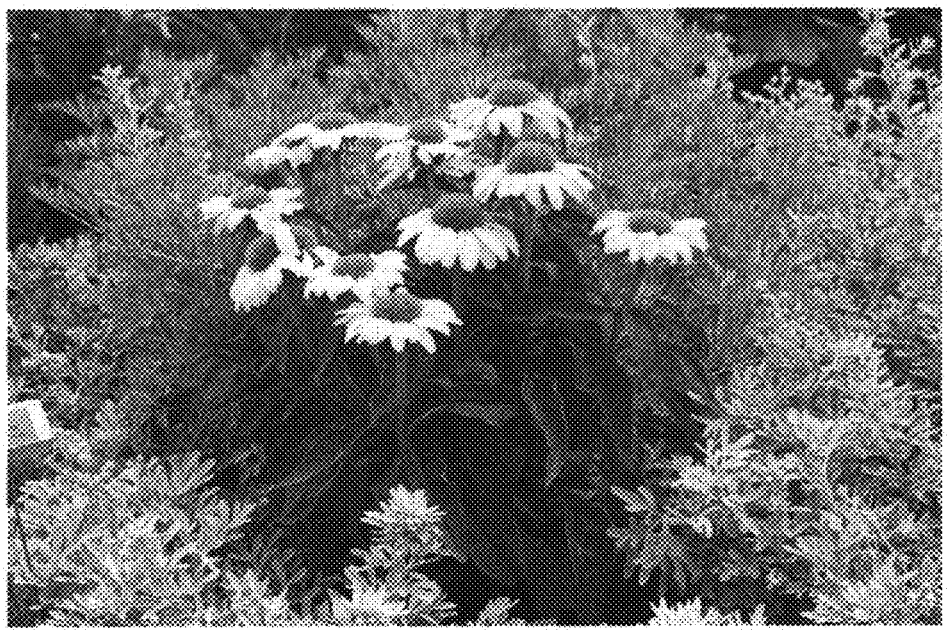
FIG. 1 shows the habit of the new plant in flower.
Figure 2:
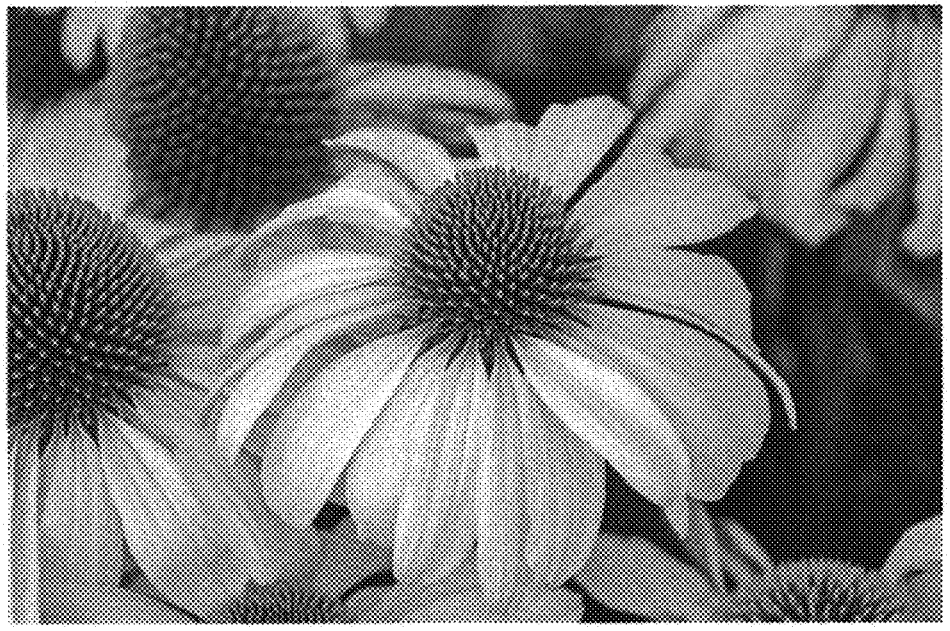
FIG. 2 shows a close up of some inflorescences of the new plant.

The following description of *Echinacea* 'The Price is White' is based on observations of two-year-old specimens grown in a full-sun trial garden with supplemental water and fertilizer in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 14-6-31 (consisting of 'Julia' U.S. Plant Pat. No. 24,629 and 'Butterfly Kisses') and male or pollen parent is 'Butterfly Kisses';

Plant habit: Multi-stemmed, heavily-branched, hardy herbaceuous perennial, flowering to about 52.0 cm tall and foliage to 38.0 cm tall and 50.0 cm wide;

Growth rate: Vigorous, finishing in 4 liter containers in about 2 months during the summer;

Roots: Cream-colored, finely branched; color nearest RHS NN155B depending on soil;

Foliage: Alternate; lanceolate; acute apex; attenuate base; margin serrulate, micro-ciliolate; puberulent abaxial and adaxial; basal leaves to about 19.0 cm long and 9.0 cm wide, cauline leaves decreasing distally, average about 14.0 cm long and 5.8 cm wide; variegation absent; rugosity absent to weak;

Leaf color: Young leaves adaxial nearest RHS NN137C, abaxial nearest RHS 147B; mature leaves adaxial between RHS 137A and RHS NN137C, abaxial nearest RHS 147B;

Foliage fragrance: Lightly herbal;

Venation: Pinnate; with two primary arcuate veins on both sides of the midrib; abaxial midrib and veins costate; glabrous adaxial, sparsely hirsutulous abaxial;

Vein color: Young and mature adaxial primary veins and midrib between RHS 146D and RHS 145A, secondary veins nearest RHS NN137A; abaxial midrib nearest RHS 145C and two primary veins nearest RHS 146D , secondary veins nearest RHS NN137A;

Petiole: Concavo-convex, strigillose adaxial and sparsely puberulent to strigillose abaxial; about 10.0 cm long and 3.0 mm wide on lowest leaves and decreasing to sessile distally; adaxial color between RHS 145B and RHS 145A in center with margins between RHS 136A and RHS NN137B, and abaxial center between RHS 146D and RHS 146C with margins between RHS 136A and RHS NN137B;

Peduncle: Densely puberulent to strigillose; cylindrical; strong stiff; to about 52.0 cm long and 9.0 mm diameter at base; quantity per plant about eight; flowering in upper 20.0 cm;

Peduncle color: Nearest RHS 146C;

Branches: Cylindrical, puberulent to strigillose; tightly angled to main stem to about 65° above horizontal: to about 24.0 cm long and 5.0 mm diameter; color nearest RHS 146C;

Inflorescence: Bracteate head, aggregate of achene; with single whorl of distinct ligulate ray florets and central disk florets in a pappus; flowering mid-summer to fall frost; initial inflorescence largest, to about 12.5 cm wide and 4.5 cm tall, average about 10.0 cm wide and 4.0 cm tall, with cones 4.8 cm across and 4.0 cm tall;

Inflorescence fragrance: Lightly sweet;

Flower persistence: Ray florets remaining affective in color for 10 to 14 days depending on temperatures, cone persistent and effective through drying on plant into winter;

Involucre: With numerous bracts; to about 76 per inflorescence in 4 whorls; arcuate downward toward peduncle;

Involucre bracts: Linear; narrowly acute apex; truncate base; micro-ciliolate margin; adaxial glabrous and lustrous; abaxial micro-puberulent; recurved greater than 90 degrees; average about 14.0 mm long and 3.5 mm across;

Involucre bract color: Adaxial center between RHS 138D and RHS 145D, margin between RHS 147A and RHS 138A; abaxial center and margin nearest RHS 138A;

Inflorescence buds with ray florets vertical and still enrolled: About 32.0 mm across and 30.0 mm tall; ray floret color nearest RHS 2D, with chaff portions nearest RHS 144A proximally and RHS 144B distally;

Ray florets: Zygomorphic; arrangement in single whorl, broadly-overlapping, typically imbricate; lanceolate, apex emarginated with two or more notches to 1.0 mm deep; base cuneate; margin entire; adaxial lustrous and glabrous; abaxial matte and glabrous; 24 to 33 per inflorescence; opening to horizontal, drooping to about 20 degrees below horizontal with maturity; sterile; ligule to 48.0 mm long and 19.0 mm wide near middle, average size 45.0 mm long, 16.5 mm wide tapering to 2 mm wide in basal 3 mm; thickened veins raised; twisting absent;

Ray ligule color: When first horizontal—adaxial between RHS 155A and RHS 155B, abaxial nearest RHS 155A with veins and light blush nearest RHS 8B, basal 3.0 mm nearest RHS 144A; before dehiscence—adaxial nearest RHS 155C and abaxial nearest RHS 155C with adaxial and abaxial base nearest RHS 144B;

Disc florets: About 250 to 350 per head; actinomorphic; perfect; synandrous; produced in raised dome, about 4.8 cm across and 4.0 cm tall; individually to about 7.5 mm long to exserted style and 2.0 mm diameter;

Corolla: Fused forming tube; outer florets to about 7.0 mm long and 1.5 mm wide, central florets about 6.0 mm long and 1.5 mm wide; fused in basal 6.0 mm, free in distal 1.0 mm; individual tepals about 0.7 mm wide at fusion; acute apex; entire margin; surfaces slightly lustrous;

Corolla tube color: Adaxial and abaxial nearest RHS 144A in distal 1.0 mm, adaxial and abaxial proximal 6.0 mm nearest RHS 145C;

Disk floret androecium: Five; synandrous;

Staminal column: About 1.0 mm wide and protrudes from corolla tube about 1.5 mm; five connate stamens;

Anthers: Fused, about 3.0 mm long and 0.7 mm diameter; color nearest RHS 200A;

Filaments: Five; attached to column; thin, about 0.1 mm diameter and about 1.0 mm long; color nearest RHS 155D;

Pollen: Globose, abundant, less 0.1 mm in diameter, RHS 17B;

Gynoecium: Single; to 7.0 mm long;

Style: About 4.0 mm long and 0.2 mm diameter; color nearest RHS 145A;

Stigma: Bifid; reflexed about 180°; about 1.5 mm long and 0.2 mm diameter; color nearest RHS 145A;

Seed: Achene; apex truncate to funiculus, with four main pappus; about 5.5 mm long and 2 mm across; funiculus about 1.0 mm across and 0.5 mm long; pappus 1.0 mm long and 0.5 mm across;

Seed color: Between RHS 199B and RHSN 199A;

Receptacle spines: One per disk florets; acicular; apex acute; base attenuate; lustrous; glabrous; to 15.0 mm long and 2.0 mm diameter;

Spine color: Adaxial and abaxial base nearest RHS NN155D, middle portion nearest RHS 138A, distally nearest RHS 23A; becoming nearest RHS 146D with flower maturity and drying to nearest RHS 200A;

Culture and performance: The new plant performs well and remains upright even when exposed to heavy rains and high winds.

Disease and pest resistance: The new plant has not been shown to have any disease or pest resistance beyond that common to Coneflower plants.

I claim:

1. A new and distinct ornamental cultivar of *Echinacea* plant named 'The Price Is White' as herein described and illustrated.

* * * * *